(12) United States Patent
Seifert

(10) Patent No.: US 10,517,744 B2
(45) Date of Patent: Dec. 31, 2019

(54) METHOD FOR CONTROLLING AN ARTIFICIAL KNEE JOINT

(71) Applicant: OTTO BOCK HEALTHCARE PRODUCTS GMBH, Vienna (AT)

(72) Inventor: Dirk Seifert, Vienna (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 12 days.

(21) Appl. No.: 15/569,060

(22) PCT Filed: Apr. 15, 2016

(86) PCT No.: PCT/EP2016/058326
§ 371 (c)(1),
(2) Date: Oct. 24, 2017

(87) PCT Pub. No.: WO2016/169846
PCT Pub. Date: Oct. 27, 2016

(65) Prior Publication Data
US 2018/0133030 A1    May 17, 2018

(30) Foreign Application Priority Data
Apr. 24, 2015   (DE) .................. 10 2015 106 391

(51) Int. Cl.
| | |
|---|---|
| *A61F 2/64* | (2006.01) |
| *A61F 2/70* | (2006.01) |
| *A61F 2/68* | (2006.01) |
| *A61F 5/01* | (2006.01) |
| *A61F 2/50* | (2006.01) |
| *A61F 2/74* | (2006.01) |

(Continued)

(52) U.S. Cl.
CPC ................. *A61F 2/68* (2013.01); *A61F 2/64* (2013.01); *A61F 5/0125* (2013.01);
(Continued)

(58) Field of Classification Search
None
See application file for complete search history.

(56) References Cited

U.S. PATENT DOCUMENTS

| | | |
|---|---|---|
| 6,755,870 B1 | 6/2004 | Biedermann et al. |
| 9,161,847 B2 | 10/2015 | Kampas et al. |

(Continued)

FOREIGN PATENT DOCUMENTS

| | | |
|---|---|---|
| CA | 2779784 C | 11/2010 |
| DE | 19859931 A1 | 7/2000 |

(Continued)

OTHER PUBLICATIONS

PCT International Search Report for PCT International Patent Application No. PCT/EP2016/058326, dated Jul. 11, 2016.

*Primary Examiner* — David H Willse
(74) *Attorney, Agent, or Firm* — Holland & Hart, LLP

(57) ABSTRACT

A method for controlling a damping change in an artificial knee joint of an orthosis or prosthesis, wherein the artificial knee joint has an upper part, a lower part mounted thereon such that it can pivot about a pivot axis, and a resistance unit which is secured on the upper part on an upper articulation point and on the lower part on a lower articulation point in order to provide a resistance to a bending or extending of the artificial knee joint, wherein an adjusting device is assigned to the resistance unit for changing the flexion resistance, wherein the resistance of the resistance unit is increased by an increasing knee angle starting from a knee angle threshold value.

18 Claims, 3 Drawing Sheets

(51) Int. Cl.
*A61F 2/76* (2006.01)
*A61F 2/66* (2006.01)

(52) U.S. Cl.
CPC ..... *A61F 2/6607* (2013.01); *A61F 2002/5006* (2013.01); *A61F 2002/5033* (2013.01); *A61F 2002/6818* (2013.01); *A61F 2002/701* (2013.01); *A61F 2002/704* (2013.01); *A61F 2002/705* (2013.01); *A61F 2002/74* (2013.01); *A61F 2002/764* (2013.01); *A61F 2002/7625* (2013.01); *A61F 2002/7635* (2013.01)

(56) References Cited

U.S. PATENT DOCUMENTS

| | | | |
|---|---|---|---|
| 2007/0027555 A1* | 2/2007 | Palmer | A61F 2/642 623/24 |
| 2007/0083272 A1* | 4/2007 | Van De Veen | A61F 2/644 623/39 |
| 2009/0171468 A1 | 7/2009 | Pusch et al. | |
| 2010/0049334 A1* | 2/2010 | Okuda | A61F 2/60 623/43 |
| 2010/0228360 A1 | 9/2010 | Pusch et al. | |
| 2011/0087339 A1 | 4/2011 | Pusch et al. | |
| 2012/0226364 A1 | 9/2012 | Kampas et al. | |
| 2012/0232674 A1 | 9/2012 | Kampas et al. | |

FOREIGN PATENT DOCUMENTS

| | | |
|---|---|---|
| DE | 102006021802 A1 | 11/2007 |
| DE | 102008008284 A1 | 8/2009 |
| DE | 102009052887 A1 | 5/2011 |
| DE | 102009052895 A1 | 5/2011 |

\* cited by examiner

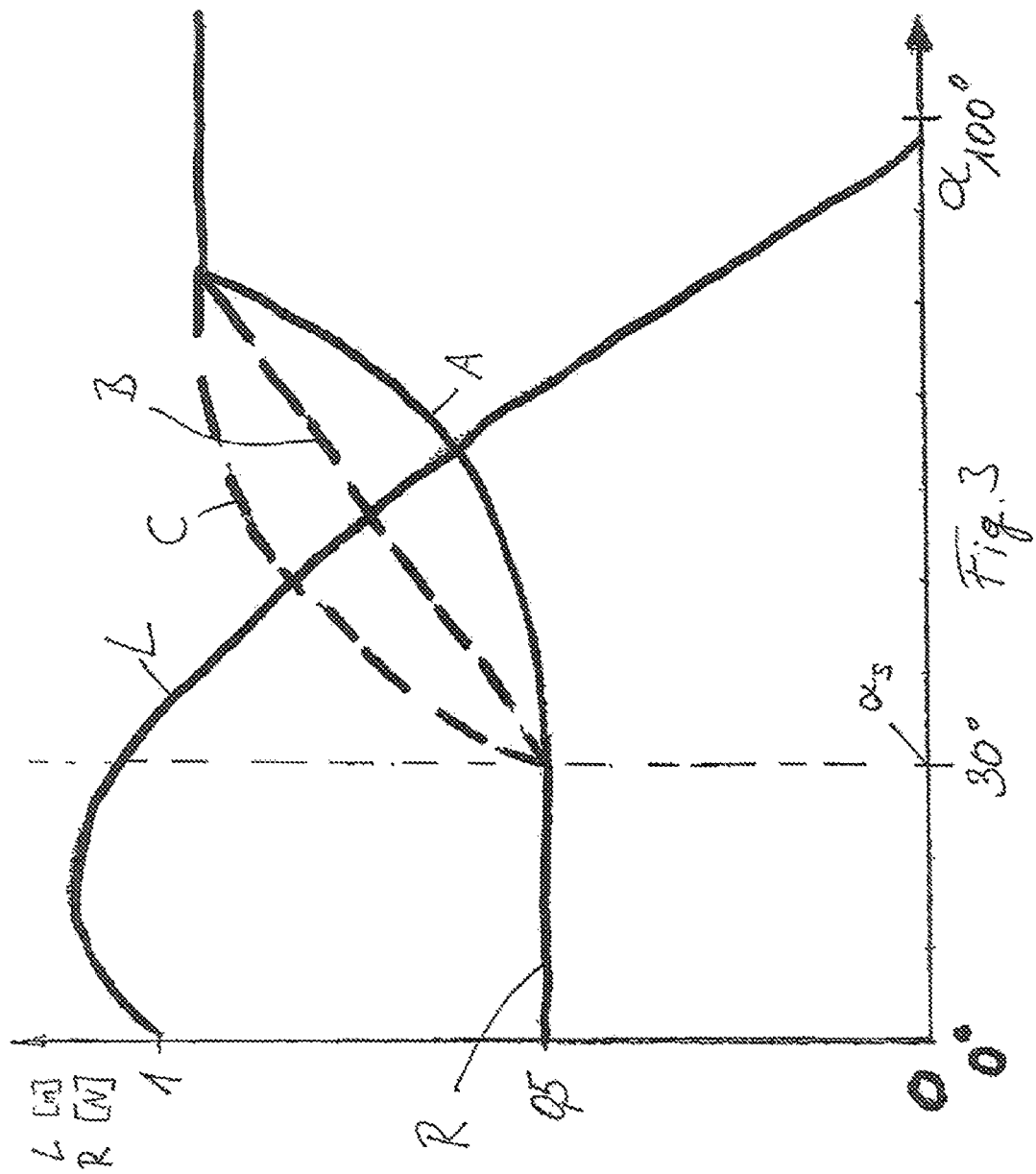

METHOD FOR CONTROLLING AN ARTIFICIAL KNEE JOINT

TECHNICAL FIELD

The invention relates to a method for controlling an artificial knee joint, in particular controlling a change in damping in an artificial knee joint which has an upper part, a lower part which is mounted on said upper part pivotably about a pivot axis, and a resistance unit, wherein the resistance unit is mounted, between the upper part and the lower part, at an upper articulation point on the upper part and at a lower articulation point on the lower part and provides flexion resistance to the flexion, wherein the resistance unit is assigned an adjustment device for changing the flexion resistance.

BACKGROUND

Knee joints for orthoses, exoskeletons or prostheses have an upper part with an upper connection part and a lower part with a lower connection part, which are articulatedly connected to one another. In general, receptacles for a thigh stump or a thigh rail are arranged on the upper connection part, whereas a lower leg tube or a lower leg rail are arranged on the lower connection part. In the simplest case, the upper part and the lower part are connected pivotably to one another by means of a uniaxial joint.

To be able to satisfy or support different requirements during the different phases of a step or during other movements or actions in a way that is as natural as possible, a resistance device is often provided which provides flexion resistance and extension resistance. The flexion resistance is used for setting how easily the lower part can be swung backwards in relation to the upper part when a force is applied. The extension resistance brakes the forward movement of the lower part and forms, inter alia, an extension limit stop.

DE 10 2008 008 284 A1 has disclosed an orthopedic knee joint with an upper part and with a lower part arranged pivotably thereon, which upper part and lower part are assigned multiple sensors, for example a flexion angle sensor, an acceleration sensor, an inclination sensor and/or a force sensor. The position of the extension limit stop is determined in a manner dependent on the sensor data.

DE 10 2006 021 802 A1 describes control of a passive prosthetic knee joint with adjustable damping in a flexion direction for adaptation of a prosthesis device with top-side connection means and with a connecting element to an artificial foot. The adaptation is made to climbing stairs, wherein a low-moment lifting of the prosthetic foot is detected, and the flexion damping is, in a lifting phase, lowered to below a level suitable for walking on a level surface. The flexion damping may be increased in a manner dependent on the change in the knee angle and in a manner dependent on the axial force acting on the lower leg.

DE 10 2009 052 887 A1 describes, inter alia, a method for controlling an orthotic or prosthetic joint with a resistance device and with sensors, wherein items of state information are provided by means of sensors during the use of the joint. The sensors detect moments or forces, wherein the sensor data of at least two of the determined variables are linked to one another by means of a mathematical operation, and in this way an auxiliary variable is calculated which is used as a basis for the control of the flexion and/or extension resistance.

According to the prior art, for the control of the change in the damping behavior, the sensor data are evaluated quantitatively, that is to say, in general, certain threshold values are predefined, in the case of the attainment or non-attainment of which the actuator is activated or deactivated, such that the resistance device provides an increased or reduced flexion or extension resistance.

DE 10 2008 024 747 A1 and DE 103 51 916 A1 have disclosed further prosthetic knee joints with which a sitting-down movement is possible.

Resistance units with articulation points or mounting points on the upper part and the lower part are necessarily installed with a spacing to the pivot axis, generally behind the pivot axis in a walking direction. The line of action of the force acting on the resistance unit between the upper articulation point and the lower articulation point thus runs with a spacing to the pivot axis in order to be able to convert the rotational movement into a translational movement of the resistance unit. Rotary hydraulic arrangements have no articulation points on the upper part and lower part.

The spacing of the force action line, running within the resistance unit between the articulation points, to the pivot axis is dependent on the knee angle. The length of a line perpendicular to the action line and running through the pivot axis is regarded as the spacing. The spacing simultaneously defines a lever arm, which is dependent on the knee angle.

It is often difficult for patients, during the movement from standing to sitting, to support their body weight using the unaided leg, such that they must often also use their hands for support.

SUMMARY

It is an object of the present invention to provide a method with which the sitting-down movement is made easier for a patient.

According to the invention, said object is achieved by means of a method having the features of the main claim; advantageous embodiments and refinements of the invention are presented in the subclaims, in the description and in the figures.

The method for controlling an artificial knee joint, in particular a change in damping in an artificial knee joint which has an upper part, a lower part which is mounted on said upper part pivotably about a pivot axis, and a resistance unit which is arranged between the upper part and the lower part, wherein the resistance unit is mounted at an upper articulation point on the upper part and at a lower articulation point on the lower part and provides flexion resistance to the flexion, wherein the resistance unit is assigned an adjustment device for changing the flexion resistance, provides that the resistance of the resistance unit is increased with increasing knee angle above a knee angle threshold value. Owing to the dependency of the resistance moment on the lever arm defined by the spacing of the force action line of the resistance unit to the pivot axis, there is the problem that, in the case of an increasing knee angle, proceeding from the point at which a maximum length of the lever arm is reached, the moment of resistance to flexion, the flexion moment, decreases if the damping resistance within the resistance unit remains constant. This arises from the geometrical relationships between the upper part, the lower part, the respective articulation points and the knee angle position. Specifically in the range of a knee flexion of over 30°, the lever arm length normally decreases, and it is therefore provided according to the invention that the flexion resistance of the resistance unit is increased with increasing flexion angle in order to lessen or compensate a decrease in the moment of resistance to flexion or in order to provide overcompensation. Thus, if a sitting-down movement is detected, then proceeding from the point at which a set threshold angle is reached, the resistance unit is changed by the adjustment device such that an increasing resistance is generated. It is thereby possible for the decreasing lever length, that is to say the decreasing spacing of the action line within the resistance unit, to be compensated, and, in the range of the knee angle in which an increased resistance moment is required during the sitting-down movement, for an increase of the resistance in the resistance unit and thus an increase of the resistance moment in relation to an unchanged resistance of the resistance unit to be provided. The method is provided for the control both of prostheses and of orthoses and exoskeletons. Where orthoses are referred to below, the statements likewise apply to the special form of the orthosis in the form of an exoskeleton.

The resistance within the resistance unit may be increased linearly, progressively or degressively. The degree of the increase, and the profile of the resistance increase, are dependent on the resistance moment to be attained. The profile and the degree of the resistance increase are likewise dependent on how the lever length changes versus the knee angle and on whether a lessening of the decrease of the resistance moment, maintenance of the set resistance moment or overcompensation of the decrease of the resistance moment should be implemented, that is to say whether the resistance moment should be increased with increasing knee angle. The resistance moment is determined from the product of the damping resistance with the lever length, that is to say the spacing of the force action line of the resistance unit to the pivot axis. The change in the resistance within the resistance unit is controlled during the sitting-down movement, whereby, overall, the resistance moment and thus the damping are increased.

That knee angle at which the spacing of the connecting line between the upper articulation point and the lower articulation point to the pivot axis is at a maximum may be set as a knee angle threshold value, above which the resistance of the resistance unit is increased.

The resistance unit may have a hydraulic or pneumatic damper with at least one flow transfer channel and with an adjustable throttle. The change in the resistance within the resistance unit is then effected by means of a reduction of the flow cross section within the throttle by means of the adjustment device.

The resistance unit may likewise have a mechanical resistance, in the case of which the moment of resistance to the flexion is imparted by means of a friction resistance. For example, the resistance of the resistance unit and thus also the flexion moment may be increased by means of an increase of the contact pressure in the mechanical resistance.

The resistance unit may be formed as an electrically operated actuator; the change in the resistance of the resistance unit may be set individually by increasing the electrical resistance within the actuator.

The resistance in the resistance unit is advantageously increased such that the flexion moment is at a maximum in a knee angle range between 70° and 90°. The flexion moment is advantageously increased, by increasing the resistance of the resistance unit, above a knee angle threshold value of 30°. Proceeding from an extended position, the knee angle is measured as an increasing knee angle with increasing flexion; the knee angle is therefore 0° in the extended position.

One refinement of the invention provides that the resistance in the resistance unit is changed in a manner inversely proportional to the profile of the lever arm change during the flexion, so as to provide a constant or virtually constant flexion moment. The resistance of the resistance unit and thus also the flexion moment are increased such that the resistance moment about the knee axis is held constant or virtually constant, such that the patient does not notice any change in the behavior of the orthosis or prosthesis. If the effective lever arm changes for example linearly, and decreases owing to the decreasing knee angle, the resistance is likewise increased linearly, such that the product of lever arm and resistance remains constant or virtually constant over the entire knee angle range. The same correspondingly applies to degressive or progressive changes in the lever arm versus the knee angle profile; progressive or degressive changes in the resistance are then provided, which correlate to the change in the lever arm. The changes in resistance may be realized by means of cam disks, other mechanical adjustment devices or by means of electronic adjustment programs. Since the characteristic of the change in lever arm does not change, and the lever arm is dependent only on the knee angle, a one-off setting of the adaptation of the change in resistance is possible.

The initial resistance is set to a level which corresponds to a stance phase damping level, that is to say a high resistance which is also at a stance phase damping level is taken as a starting point, such that, already at the start of the flexion, a resistance and flexion moment prevail which are high enough to provide the patient with a feeling of safety. The initial value may lie between 40% and 70% of the maximum resistance.

The resistance unit may for example be configured as an actuator, for example as a hydraulic, pneumatic, magnetorheological, magnetic, electrical, mechanical or electromagnetic resistance unit. In the case of hydraulic or pneumatic resistance units, flow transfer channels are closed, such that said flow transfer channels can no longer allow medium to flow from an extension chamber into a flexion chamber. In this way, the flow of the medium between the extension chamber and the flexion chamber can possibly also be prevented entirely. In the case of mechanical resistance devices, it is for example the case that the friction is increased to such an extent that no further flexion is possible. The same applies to electrically actuated resistance units.

Use may also be made of actuators which both actively introduce energy into the system and also conversely extract energy from the system, and thereby act as a resistance unit. Actuators may for example be formed as electric motors, hydraulic or pneumatic pumps or piezoelectric elements.

BRIEF DESCRIPTION OF THE DRAWINGS

An exemplary embodiment of the invention will be discussed in more detail below on the basis of the appended figures. In the figures.

DETAILED DESCRIPTION

Figure 1:
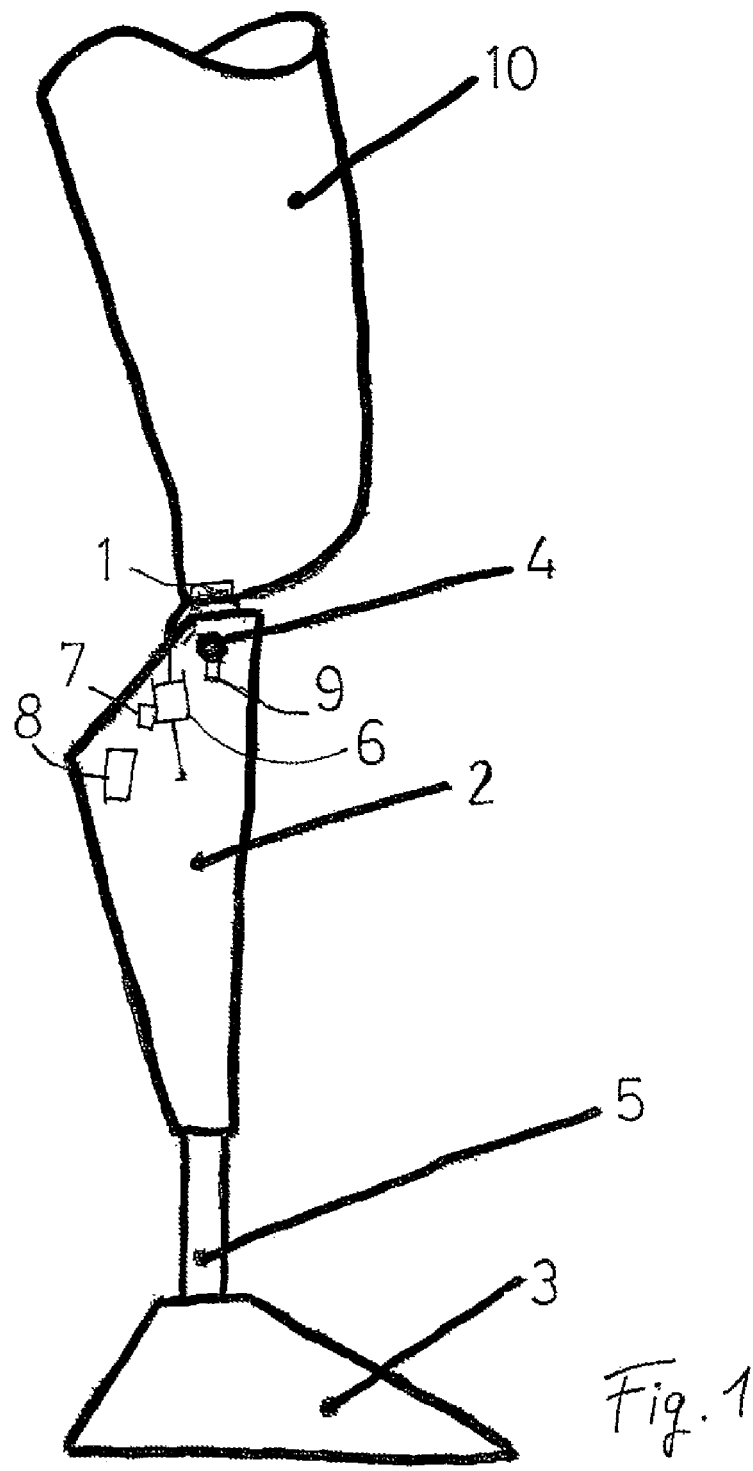
FIG. 1—shows a schematic illustration of a prosthesis.

FIG. 1 illustrates, in a schematic illustration, a leg prosthesis with an upper part 1 to which a thigh socket 10 for receiving a thigh stump is fastened. A lower part 2 designed as a lower leg part is arranged pivotably on the upper part 1. The lower part 2 is mounted on the upper part 1 pivotably about a pivot axis 4. The lower part 2 has a lower leg tube 5, to the distal end of which there is fastened a prosthetic foot 3 in which there may be accommodated a device for determining the axial force acting on the lower leg tube 5 and the ankle moment acting about the fastening point of the prosthetic foot 3 to the lower leg tube 5.

In or on the lower part 2 there is arranged a resistance device 6 which may be formed for example as a damper or actuator and which is supported between the upper part 1 and the lower part 2 in order to provide an adjustable extension resistance and flexion resistance. The resistance device 6 is assigned an adjustment device 7, for example a motor, a magnet or some other actuator, by means of which the respective resistance R within the resistance device 6 can be varied. If the resistance device 6 is formed as a hydraulic damper or pneumatic damper, it is possible by means of the adjustment device 7 for the respective flow cross section of a flow transfer channel to be increased or decreased in size. It is likewise possible for the flow resistance to be varied in some other way by means of the adjustment device 7. This may be realized for example by opening or closing valves or changing viscosities or magnetorheological characteristics. If the resistance device is formed as an electric motor operating as a generator, it is possible for an increase or decrease in the respective resistances to flexion or extension to be set through variation of the electrical resistance.

To be able to activate or deactivate the adjustment device 7, a control device 8 is assigned to the lower part 2, in particular is accommodated in a lower leg trim, by means of which control device a corresponding activation or deactivation signal is output to the adjustment device 7. The adjustment device 7 is activated or deactivated on the basis of sensor data, and the sensor data are provided by one or more sensors 9 which are arranged on the artificial knee joint. These may be angle sensors, acceleration sensors and/or force sensors. The sensors 9 are connected to the control device 8, for example by cable or by means of a wireless transmission device. In the exemplary embodiment illustrated, the sensor 9 is formed inter alia as a knee angle sensor.

The entire step cycle from the heel strike to the new, next heel strike HS, and thus also the entire swing phase with the swing phase extension and the swing phase flexion, is monitored by means of the sensors 9.

Figure 2:
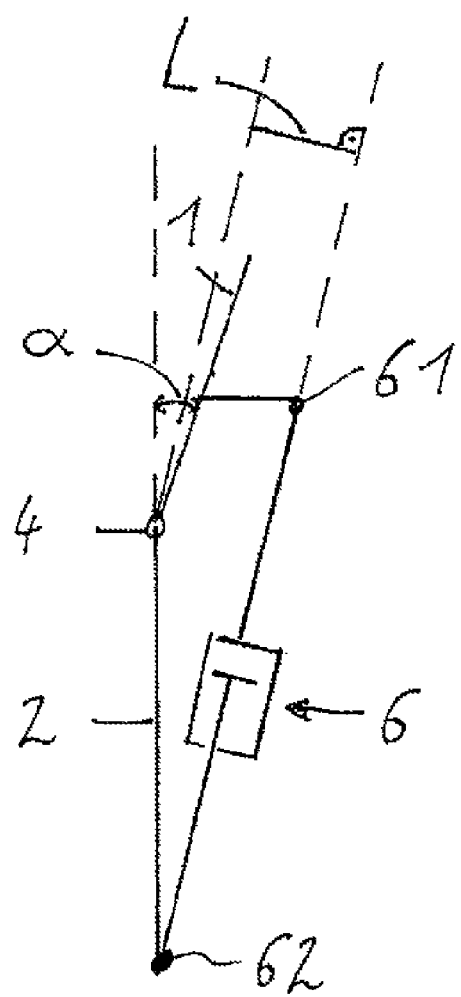
FIG. 2—shows a schematic illustration of the damper arrangement on the artificial joint, and FIG. 3—shows a schematic illustration of the resistance unit between upper part and lower part.

FIG. 2 shows, in a schematic illustration, the artificial knee joint with the upper part 1, the lower part 2, the pivot axis 4 and the resistance unit 6 arranged in between. The resistance unit 6 is illustrated as a linearly acting resistance unit. The resistance unit 6 provides a resistance R, in the form of a resistance force, to the flexion of the artificial knee joint about the pivot axis 4. The resistance unit 6 is fixed at an upper articulation point 61 to the upper part 1 and at a lower articulation point 62 to the lower part 2. In the exemplary embodiment illustrated, the resistance unit 6 is a hydraulic or pneumatic damper, though other linearly acting resistance units or devices which provide a resistance R to a displacement of two components relative to one another are in principle also suitable for being used as a resistance unit. The force action line of the resistance unit runs through a connecting line between the upper articulation point 61 and the lower articulation point 62.

FIG. 2 illustrates the spacing L of the action line from the pivot axis 6. The spacing L is determined from the spacing of the action line between the upper articulation point 61 and the lower articulation point 62 of the resistance unit 6 to an imaginary line parallel thereto and passing through the pivot axis 4. In a fully extended position, in the extended position of the artificial knee joint, the upper part 1 and the lower part 2 are substantially parallel to one another; the knee angle $\alpha$ is 0°. To make it possible for damping to be realized in the first place, it is necessary even in the fully extended position for a spacing L to be present between the action line of the resistance unit 6 and the pivot axis 4. Normally, the knee joint has a pivot range of greater than 100° in order to permit comfortable sitting and possibly also kneeling. If a maximum spacing were present in the fully extended position of the artificial knee, a dead center position would be reached after flexion of the artificial knee through 90°. That is to say, in the case of a linearly acting damper, a movement reversal would occur; in the region of the top dead center, the spacing would be zero, and thus the maximum resistance moment that can be imparted would also be zero, because the moment of resistance to flexion is determined from the product of the resistance force of the resistance unit 6 with the spacing L as lever arm.

FIG. 3 shows the profile, plotted versus the knee angle $\alpha$, of a normalized lever arm value, wherein the lever arm L is assumed to be 1 in the case of a knee angle $\alpha$ of 0°, that is to say in the case of a fully extended position. Likewise plotted is the profile of the resistance R of the resistance unit 6 versus the knee angle $\alpha$.

The profile of the lever arm L initially increases until the spacing to the pivot axis 4 reaches a maximum. In the illustrated exemplary embodiment, this is the case at a knee angle $\alpha$ of approximately 15°. Subsequently, owing to the approximately circular movement of the upper articulation point 6 about the pivot axis 4, the value of the spacing L decreases until, at a knee angle of approximately 100°, the connecting line between the upper articulation point 61 and the lower articulation point 62 runs through the pivot axis 4. If the knee joint is flexed further, this leads to a movement reversal within the resistance unit 6, for example to a reversal of a hydraulic or pneumatic piston, of a mechanical resistance, for example a friction brake, or of an electrically operating actuator.

If the damper resistance R were to remain constant, it would be the case, with an increasing pivot angle $\alpha$, that only a decreasing resistance moment can be provided proceeding from the point at which the maximum length of the effective lever arm L is reached, because the effective lever decreases. According to the invention, it is therefore provided that, in a manner dependent on the knee angle $\alpha$, proceeding from the point at which a threshold value $\alpha_s$ is reached, the damper resistance is increased, for example by virtue of an initially semi-closed valve in a hydraulic or pneumatic resistance unit 6 being progressively closed. In the exemplary embodiment illustrated, provision is not made for the valve to be fully shut off, such as would be the case at a value 1.

In the illustration of FIG. 3, three different curves of the change in resistance are shown. The first curve A with a progressive profile up to a knee angle of 90° has the effect that a maximum resistance moment prevails approximately in the range of a knee angle position between 70° and 90°.

The curve profile B shows a linear increase of the damping resistance, whereby initially an increasing resistance moment is generated owing to a relatively slow decrease of the lever length L; during the further course of the knee flexion, the resistance moment then decreases.

The characteristic curve C gives rise to an initially increasing resistance moment which, after a maximum value is reached at approximately 45°, is progressively decreased owing to the degressive curve.

The control method serves for the adaptation of the resistance moment to the requirements when sitting down. To identify whether a patient wishes to perform a sitting-down function or is performing the sitting-down movement, it is possible either for a corresponding control program to be manually selected or, by means of various sensors, for a distinction to automatically be performed on the basis of the evaluation of sensor data. Use may also be made of acceleration sensors, position sensors, force sensors and absolute angle sensors, which allow a distinction to be made between sitting down, walking on a level surface, walking downhill, walking on inclined surfaces or climbing stairs.

With the method according to the invention, it is possible for the mechanism of the artificial knee joint to be left unchanged; only the damper resistance R is increased, for example by virtue of a liquid passage being increasingly shut off, by means of an increase in a friction value, or by means of an increase in an electrical resistance. This has the effect that, in the case of an increasing knee angle, the moment of resistance to flexion is kept high.

The invention claimed is:

1. A method for controlling a change in damping in an artificial knee joint of an orthosis or prosthesis, the method comprising;
   providing an artificial knee joint having an upper part, a lower part which is mounted on the upper part pivotably about a pivot axis, and a resistance unit which is fastened to the upper part at an upper articulation point and to the lower part at a lower articulation point to provide a resistance to a flexion or extension of the artificial knee joint, the resistance unit being assigned an adjustment device to change the flexion resistance;
   increasing the resistance with the resistance unit with an increasing knee angle above a knee angle threshold value;
   wherein a knee angle at which a spacing between the pivot axis and a connecting line between the upper articulation point and the lower articulation point is at a maximum is set as the knee angle threshold value.

2. The method as claimed in claim 1, wherein the resistance of the resistance unit is increased linearly, progressively or degressively with increasing knee angle.

3. The method as claimed in claim 1, wherein the resistance unit has a hydraulic or pneumatic damper with at least one flow transfer channel and an adjustable throttle.

4. The method as claimed in claim 1, wherein the resistance unit has a mechanical resistance.

5. The method as claimed in claim 1, wherein the resistance unit has an electrically operated actuator.

6. The method as claimed in claim 1, wherein the resistance of the resistance unit increases such that the flexion moment is at a maximum in a knee angle range between 70° and 90°.

7. The method as claimed in claim 1, wherein the resistance of the resistance unit is increased above a knee angle threshold value of 30°.

8. The method as claimed in claim 1, wherein the resistance of the resistance unit is changed in a manner inversely proportional to a profile of a lever arm change during the flexion to provide a constant or virtually constant flexion moment.

9. The method as claimed in claim 1, wherein an initial resistance is set to a level which corresponds to a stance phase damping level.

10. A method to control a change in damping in an artificial knee joint of an orthosis or prosthesis, the method comprising;
    providing an artificial knee joint having an upper part, a lower part pivotally mounted to the upper part, and a resistance unit fastened to the upper part at an upper articulation point and to the lower part at a lower articulation point;
    providing a resistance to flexion or extension of the artificial knee joint with the resistance unit;
    increasing the resistance with the resistance unit with an increasing knee angle above a knee angle threshold value;
    setting as the knee angle threshold value a knee angle at which a spacing between the pivot axis and a connecting line between the upper articulation point and the lower articulation point is at a maximum.

11. The method as claimed in claim 10, wherein the resistance of the resistance unit is increased linearly, progressively or degressively with increasing knee angle.

12. The method as claimed in claim 10, wherein the resistance unit has a hydraulic or pneumatic damper with at least one flow transfer channel and an adjustable throttle.

13. The method as claimed in claim 10, wherein the resistance unit has a mechanical resistance.

14. The method as claimed in claim 10, wherein the resistance unit has an electrically operated actuator.

15. The method as claimed in claim 10, wherein the resistance of the resistance unit increases such that the flexion moment is at a maximum in a knee angle range between 70° and 90°.

16. The method as claimed in claim 10, wherein the resistance of the resistance unit is increased above a knee angle threshold value of 30°.

17. The method as claimed in claim 10, wherein changing the resistance of the resistance unit in a manner inversely proportional to a profile of a lever arm change during the flexion to provide a constant or virtually constant flexion moment.

18. The method as claimed in claim 10, wherein an initial resistance is set to a level which corresponds to a stance phase damping level.

* * * * *